(12) United States Patent
Andersch et al.

(10) Patent No.: US 8,389,440 B2
(45) Date of Patent: Mar. 5, 2013

(54) SYNERGISTIC INSECTICIDE MIXTURES

(75) Inventors: Wolfram Andersch, Bergisch Gladbach (DE); Christoph Erdelen, Leichlingen (DE); Angelika Lubos-Erdelen, legal representative, Leichlingen (DE); Peter Jeschke, Bergisch Gladbach (DE); Thomas Bretschneider, Lohmar (DE)

(73) Assignee: Bayer Cropscience AG, Monheim (DE)

( * ) Notice: Subject to any disclaimer, the term of this patent is extended or adjusted under 35 U.S.C. 154(b) by 576 days.

(21) Appl. No.: 10/504,773

(22) PCT Filed: Feb. 10, 2003

(86) PCT No.: PCT/EP03/01281
§ 371 (c)(1),
(2), (4) Date: Jan. 26, 2005

(87) PCT Pub. No.: WO03/070001
PCT Pub. Date: Aug. 28, 2003

(65) Prior Publication Data
US 2006/0063829 A1 Mar. 23, 2006

(30) Foreign Application Priority Data
Feb. 21, 2002 (DE) .................. 102 07 241

(51) Int. Cl.
*A01N 25/26* (2006.01)
*A01N 43/02* (2006.01)
*A01N 43/00* (2006.01)
*A61K 31/33* (2006.01)

(52) U.S. Cl. .......................... 504/100; 504/140; 514/183
(58) Field of Classification Search ................... 514/183
See application file for complete search history.

(56) References Cited

U.S. PATENT DOCUMENTS

| | | | |
|---|---|---|---|
| 3,313,684 A | 4/1967 | Schegk et al. ................. | 167/30 |
| 4,310,519 A | 1/1982 | Albers-Schonberg et al. ........................ | 424/181 |
| 4,427,663 A | 1/1984 | Mrozik ........................ | 424/180 |
| 4,510,098 A | 4/1985 | Crosby ..................... | 260/465 D |
| 4,510,160 A | 4/1985 | Robson ........................ | 514/521 |
| 4,782,174 A | 11/1988 | Fuchs et al. ................... | 558/354 |
| 4,874,749 A | 10/1989 | Mrozik ........................ | 514/30 |
| 5,288,710 A | 2/1994 | Cvetovich .................... | 514/30 |
| 5,708,170 A | 1/1998 | Annis et al. ................... | 544/212 |
| 2004/0266626 A1* | 12/2004 | Schrof et al. ................. | 504/361 |

FOREIGN PATENT DOCUMENTS
EP 0 979 606 2/2000

OTHER PUBLICATIONS

Journal of Organic Chemistry, vol. 59, (month unavailable) 1994. Raymond J. Cvetovich et al, pp. 7704-7708, "Syntheses of 4"-epi-Amino-4"eoxyavermectins B₁".

The Pesticide Manual, 11ᵗʰ edition, (month unavailable) 1997, pp. 3-5, "Abamectin".
The Pesticide Manual, 11ᵗʰ edition, (month unavailable) 1997, pp. 813-815, "Methiocarb".
The Pesticide Manual, 11ᵗʰ Edition, (month unavailable) 1997, p. 295-297, "Beta-cyfluthrin".
The Pesticide Manual, 11ᵗʰ Edition, (month unavailable) 1997, p. 300-302, Lambda-cyhalothrin.
The Pesticide Manual, 11ᵗʰ Edition, (month unavailable) 1997, p. 453-454, "DPX-JW062 and DPX-MP062".
Chem. Ind., 37, (month unavailable) 1985, pp. 730-732, Harry R. Ungerer, "Schiffsfarben—eine Spezialität der seenahen Lackindustrie".
Agricultural and Food Chemistry, vol. 9, No. 1, (month unavailable) 1961, pp. 30-39, C.P. Carpenter et al, Mammalian Toxicity of 1-Naphthyl-*N*-methylcarbamate (Sevin Insecticide).
Database CA 'Online! Chemical Abstracts Service, Columbus, Ohio, US; Bretschneider, Thomas et al: Synergistic insecticide mixtures XP002240655 accession No. STN Database accession No. 133:248393 Zusammenfassung CAS-RN 295785-87-4 & DE 199 13 174 A (Bayer A.-G., Germany Sep. 28, 2000.
Database CA 'Online! Chemical Abstracts Service, Columbus, Ohio, US; Saito, Shigeru, Synergistic insecticidal compositions containing (trifluoromethyl)pyridin derivative and pest control method XP002240656 accession No. 134:52652 Zusammenfassung CAS-RN 313706-93-3 & WO 2001 000027 A (Sumitomo Chemical Company, Limited, Japan) Jan. 4, 2001.
Database CA 'Online! Chemical Abstracts Service, Columbus, Ohio, US; Kawahara, Nobuyuki et al: Synergistic insecticides containing (tetrahydrofurylmethyl)nitroguanidine: XP002240657 accession No. STN Database accession No. 125:268220 CAS-RN 182426-42-2, 182426-43-3, 182426-45-5 Zusammenfassung & JP 08 217606 A (Mitsui Toatsu Chemicals, Japan) Aug. 27, 1996.
Database WPI Section Ch, Week 199644 Derwent Publications Ltd., London, GB; AN 1996-439409 XP002178795 & JP 08 217609 A (Mitsui Toatsu Chem Inc) Aug. 27, 1996.
Database WPI Section Ch, Week 199644 Derwent Publications Ltd., London, GB; AN 1996-439410 XP002178796 & JP 08 217610 A (Mitsui Toatsu Chem Inc) Aug. 27, 1996.

* cited by examiner

*Primary Examiner* — Alton Pryor
(74) *Attorney, Agent, or Firm* — Baker Donelson Bearman Caldwell & Berkowitz

(57) ABSTRACT

The invention relates to insecticidal mixtures containing the compound of the formula (I)

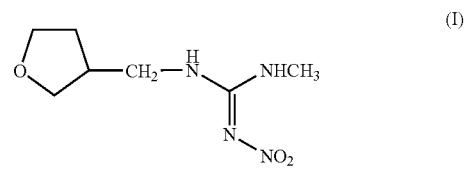

and at least one further known active compound from the series abamectin, emamectin and/or emamectin benzoate, methiocarb, β-cyfluthrin, lambda-cyhalothrin, and indoxacarb, and further relates to the use of these mixtures for controlling animal pests.

7 Claims, No Drawings

SYNERGISTIC INSECTICIDE MIXTURES

The present patent application has been filed under 35 U.S.C. 371 as a national stage application of PCT/EP03/01281, filed Feb. 10, 2003, which was published in German as International Patent Publication WO 03/070001 on Aug. 28, 2003, and is entitled to the right of priority of German Patent Application 102 07 241.8, filed Feb. 21, 2002.

The present invention relates to new active compound combinations which contain firstly the known active compound dinotefuran and secondly at least one further known insecticidal active compound and which have very good insecticidal and acaricidal properties.

It is already known that dinotefuran, of the formula

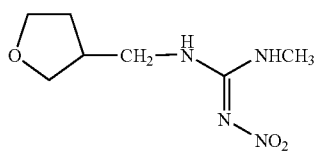

(I)

can be employed for controlling animal pests, in particular insects (cf. EP-A-0 649 845). While the activity of this compound is good, it leaves something to be desired in some cases when used at low application rates or against specific pests.

It has also been disclosed that the compounds abamectin (II) (DE 2 717 040), emamectin (III) and/or emamectin benzoate (IIIa) (EP 089 202), methiocarb (IV) (U.S. Pat. No. 3,313,684), β-cyfluthrin (V) (EP 206 149), lambda-cyhalothrin (VI) (EP 106 469) and indoxacarb (VII) (WO 92/11 249) can be used for controlling insects and/or acarina.

It has now been found that mixtures containing dinotefuran, of the formula (I)

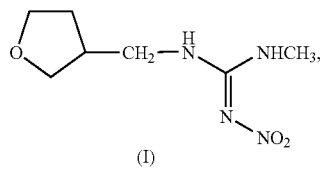

(I)

and at least one of the compounds (II), (III), (IIIa), (IV), (V), (VI) and (VII) are synergistically active and are suitable for controlling animal pests. Owing to this synergism, markedly lower amounts of active compound may be used, that is to say the effect of the mixture exceeds the effect of the individual components.

The ratio of the compound of the formula (I) employed to the compounds of the formulae (II) to (VII), and the total amount of the mixture to be employed, depend on the species and the occurrence of the insects or acarina. The optimal ratios and overall rates used can be determined for each application by test series.

A preferred mixture according to the invention contains the active compound dinotefuran, of the formula (I), and abamectin (II). Abamectin is also known from "The Pesticide Manual", 11$^{th}$ Edition, British Crop Protection Council, 1997, page 3. The terms abamectin and avermectin are used synonymously in the present patent application.

In this mixture, the ratio of the active compounds to each other may be varied within a substantial range. The weight ratio of dinotefuran to abamectin is preferably between 1:1 and 50:1, in particular between 5:1 and 25:1.

A further preferred mixture according to the invention contains the active compound dinotefuran, of the formula (I), and emamectin (III) and/or emamectin benzoate (IIIa). Emamectin and salts of emamectin are also known as MK-244 from Journal of Organic Chemistry, Vol. 59 (1994), 7704-7708, U.S. Pat. Nos. 4,874,749, 5,288,710 and EP-00 089 202.

In this mixture, the ratio of the active compounds to each other may be varied within a substantial range. The weight ratio of dinotefuran to emamectin and/or emamectin benzoate is preferably between 1:1 and 500:1, in particular between 100:1 and 500:1.

A further preferred mixture according to the invention contains the active compound dinotefuran, of the formula (I), and methiocarb (IV). Methiocarb (IV) is also known from "The Pesticide Manual", 11th Edition, British Crop Protection Council, 1997, page 813.

In this mixture, the ratio of the active compounds to each other may be varied within a substantial range. The weight ratio of dinotefuran to methiocarb is preferably between 1:1 and 1:10, in particular between 1:1 and 1:5.

A further preferred mixture according to the invention contains the active compound dinotefuran of the formula (I) and β-cyfluthrin (V). β-Cyfluthrin is also known from "The Pesticide Manual", 11th Edition, British Crop Protection Council, 1997, page 295.

In this mixture, the ratio of the active compounds to each other may be varied within a substantial range. The weight ratio of dinotefuran to β-cyfluthrin is preferably between 1:1 and 10:1, in particular between 1:1 and 6:1.

A further preferred mixture according to the invention contains the active compound dinotefliran of the formula (I) and lambda-cyhalothrin (VI). Lambda-cyhalothrin (VI) is also known from "The Pesticide Manual", 11th Edition, British Crop Protection Council, 1997, page 300.

In this mixture, the ratio of the active compounds to each other may be varied within a substantial range. The weight ratio of dinotefuran to lambda-cyhalothrin is preferably between 1:1 and 10:1, in particular between 1:1 and 6:1.

A further preferred mixture according to the invention contains the active compound dinotefuran of the formula (I) and indoxacarb (VII). Indoxacarb (VII) is also known from "The Pesticide Manual", 11th Edition, British Crop Protection Council, 1997, page 453.

In this mixture, the ratio of the active compounds to each other may be varied within a substantial range. The weight ratio of dinotefuran to indoxacarb is preferably between 1:1 and 1:10, in particular between 1:1 and 1:5.

The active compound combinations are well tolerated by plants, demonstrate advantageous toxicity to warm-blooded species and are suitable for controlling animal pests, in particular insects, arachnids and nematodes, which are found in agriculture, in forestry, in the protection of stored products and materials and in the hygiene sector. They can preferably be employed as crop protection agents. They are active against normally sensitive and resistant species and against all or individual developmental stages. The abovementioned pests include:

From the order of the *Isopoda*, for example, *Oniscus asellus, Armadillidium vulgare, Porcellio scaber.*

From the order of the *Diplopoda*, for example, *Blaniulus guttulatus.*

From the order of the *Chilopoda*, for example, *Geophilus carpophagus, Scutigera* spp.

From the order of the *Symphyla*, for example, *Scutigerella immaculate*.

From the order of the *Thysanura*, for example, *Lepisma saccharina*.

From the order of the *Collembola*, for example, *Onychiurus armatus*.

From the order of the *Orthoptera*, for example, *Acheta domesticus, Gryllotalpa* spp., *Locusta migratoria migratorioides, Melanoplus* spp., *Schistocerca gregaria*.

From the order of the *Blattaria*, for example, *Blatta orientalis, Periplaneta americana, Leucophaea maderae, Blattella germanica*.

From the order of the *Dermaptera*, for example, *Forficula auricularia*.

From the order of the *Isoptera*, for example, *Reticulitermes* spp.

From the order of the *Phthiraptera*, for example, *Pediculus humanus corporis, Haematopinus* spp., *Linognathus* spp., *Trichodectes* spp., *Damalinia* spp.

From the order of the *Thysanoptera*, for example, *Hercinothrips femoralis, Thrips tabaci, Thrips palmi, Frankliniella occidentalis*.

From the order of the *Heteroptera*, for example, *Eurygaster* spp., *Dysdercus intermedius, Piesma quadrata, Cimex lectularius, Rhodnius prolixus, Triatoma* spp.

From the order of the *Homoptera*, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the *Lepidoptera*, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae*.

From the order of the *Coleoptera*, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus*.

From the order of the *Hymenoptera*, for example, *Diprion* spp., *Hoplocampa* spp., *Lasius* spp., *Monomorium pharaonis, Vespa* spp.

From the order of the *Diptera*, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the *Siphonaptera*, for example, *Xenopsylla cheopis, Ceratophyllus* spp.

From the class of the *Arachnida*, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

All plants and plant types may be treated in accordance with the invention. Plants are understood as meaning, in the present context, all plants and plant populations such as desired and undesired wild plants or crop plants (including naturally occurring crop plants). Crop plants may be plants which can be obtained by conventional breeding and optimization methods or by biotechnological and recombinant methods or combinations of these methods, including the transgenic plants and including the plant varieties capable of protection or not by Plant Breeders' Rights. Plant parts are understood as meaning all aerial and subterranean plants and organs of the plants, such as shoot, leaf, flower and root, examples which may be mentioned being leaves, needles, stalks, stems, flowers, fruiting bodies, fruits and seeds, and roots, tubers and rhizomes. The plant parts also include harvested material and vegetative and generative propagation material, for example cuttings, tubers, rhizomes, shoots and seeds.

The treatment according to the invention of the plant and plant parts with the active compound combinations is effected directly or by application to the surroundings, environment or store by the customary treatment methods, for example by dipping, spraying, atomizing, fogging, spreading, brushing on and, in the case of propagation material, in particular seeds, furthermore by applying one or more coats.

The active compound combinations can be converted into the customary formulations such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surface-active agents, that is, emulsifiers and/or dispersants and/or foam formers.

In the case of the use of water as extender, organic solvents can, for example, also be used as cosolvents. Suitable as liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, as well as water.

Suitable solid carriers are:

for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifiers and/or foam formers are: for example non-ionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, and protein hydrolysates; suitable dispersants are: for example lignin-sulphite waste liquors and methylcellulose.

Adhesives such as carboxymethylcellulose, and natural and synthetic polymers in the form of powders, granules or latices, such as gum arabic, polyvinyl alcohol and polyvinyl acetate, and natural phospholipids such as cephalins and lecithins and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally contain between 0.1 and 95% by weight of active compound, preferably between 0.5 and 90%.

The active compound combinations according to the invention, in commercially available formulations and in the use forms prepared from these formulations, may be present as a mixture with other active compounds such as insecticides, attractants, sterilants, bactericides, acaracides, nematicides, fungicides, growth regulators or herbicides. Insecticides include, for example, phosphoric esters, carbamates, carboxylic esters, chlorinated hydrocarbons, phenylureas, substances produced by microorganisms and the like.

Examples of suitable components in mixtures are the following:

Fungicides:

aldimorph, ampropylfos, ampropylfos-potassium, andoprim, anilazin, azaconazole, azoxystrobin, benalaxyl, benodanil, benomyl, benzamacryl, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezin, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromid, fluquinconazole, flurprimidol, flusilazole, flusulfamide, flutolanil, flutriafol, folpet, fosetyl-alminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadin, iminoctadin albesilate, iminoctadin triacetate, iodocarb, ipconazole, iprobenfos (IBP), iprodione, irumamycin, isoprothiolan, isovaledione, kasugamycin, kresoxim-methyl, copper preparations such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidon, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforin, triticonazole, uniconazole, validamycin A, vinclozolin, viniconazole, zarilamid, zineb, ziram and Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)phenyl]methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxyphenylacetamide, 1-isopropyl{2-methyl-1-[[[1-(4-methylphenyl)ethyl]amino]carbonyl]propyl}-carbamate, 1-(2,4-dichlorophenyl)-2-(1H-1,2,4-triazol-1-yl)ethanone O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)sulphonyl]-4-methylbenzene, 1-[[2-(2,4-dichlorophenyl)-1,3-dioxolan-2-yl]methyl]-1H-imidazole, 1-[[2-(4-chlorophenyl)-3-phenyloxiranyl]methyl]-1H-1,2,4-triazole,
1-[1-[2-[(2,4-dichlorophenyl)methoxy]phenyl]ethenyl]-1H-imidazole, 1-methyl-5-nonyl-2-(phenylmethyl)-3-pyrrolidinol,
2',6'-dibromo-2-methyl-4'-trifluoromethoxy-4'-trifluoromethyl-1,3-thiazole-5-carboxanilide,
2,2-dichloro-N-[1-(4-chlorophenyl)ethyl]-1-ethyl-3-methylcyclopropane-carboxamide,
2,6-dichloro-5-(methylthio)-4-pyrimidinylthiocyanate,
2,6-dichloro-N-(4-trifluoromethylbenzyl)benzamide,
2,6-dichloro-N-[[4-(trifluoromethyl)phenyl]methyl]benzamide,
2-(2,3,3-triiodo-2-propenyl)-2H-tetrazole,
2-[(1-methylethyl)sulphonyl]-5-(trichloromethyl)-1,3,4-thiadiazole,
2-[[6-deoxy-4-O-(4-O-methyl-β-D-glycopyranosyl)-a-D-glucopyranosyl]amino]-4-methoxy-1H-pyrrolo[2,3-d]pyrimidine-5-carbonitrile,
2-aminobutane,
2-bromo-2-(bromomethyl)pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)acetamide,
2-phenylphenol(OPP),
3,4-dichloro-1-[4-(difluoromethoxy)phenyl]-1H-pyrrole-2,5-dione,
3,5-dichloro-N-[cyano[(1-methyl-2-propynyl)oxy]methyl]benzamide,
3-(1,1-dimethylpropyl-1-oxo)-1H-indene-2-carbonitrile,
3-[2-(4-chlorophenyl)-5-ethoxy-3-isoxazolidinyl]pyridine,
4-chloro-2-cyano-N,N-dimethyl-5-(4-methylphenyl)-1H-imidazole-1-sulphonamide,
4-methyltetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
N-2-[(phenylamino)carbonyl]-9H-xanthene-9-carbohydrazide,
bis-(1-methylethyl)-3-methyl-4-[(3-methylbenzoyl)oxy]-2,5-thiophenedicarboxylate,
cis-1-(4-chlorophenyl)-2-(1H-1,2,4-triazol-1-yl)cycloheptanol,
cis-4-[3-[4-(1,1-dimethylpropyl)phenyl-2-methylpropyl]-2,6-dimethylmorpholine hydrochloride,
ethyl [(4-chlorophenyl)azo]cyanoacetate,
potassium hydrogencarbonate,
sodium methanetetrathiolate,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methylcyclohexanecarboxamide,
N-(2,6-dimethylphenyl)-2-methoxy-N-(tetrahydro-2-oxo-3-furanyl)acetamide,
N-(2,6-dimethylphenyl)-2-methoxy-N-(tetrahydro-2-oxo-3-thienyl)acetamide,
N-(2-chloro-4-nitrophenyl)-4-methyl-3-nitrobenzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)acetamide,
N-(6-methoxy)-3-pyridinyl)cyclopropanecarboxamide,
N-[2,2,2-trichloro-1-[(chloroacetyl)amino]ethyl]benzamide,
N-[3-chloro-4,5-bis(2-propinyloxy)phenyl]-N'-methoxymethaneimidamide,
sodium N-formyl-N-hydroxy-DL-alaninate,
O,O-diethyl[2-(dipropylamino)-2-oxoethyl]ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran)-3'-one.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:
abamectin, acephate, acetamiprid, acrinathrin, alanycarb, aldicarb, aldoxycarb, alphacypermethrin, alphamethrin, amnitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cis-permethrin, clocythrin, cloethocarb, clofentezine, clothianidin, cyanophos, cyclopene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoate, dimethylvinphos, diofenolan, disulfoton, docusate sodium, dofenapyn,
eflusilanate, emamectin, empenthrin, endosulfan, *Entomophthora* spp., esfenvalerate, ethiofencarb, ethiprole, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses
lambda-cyhalothrin, lufenuron
malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos,
naled, nitenpyram, nithiazine, novaluron
omethoate, oxamyl, oxydemethon M
*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen, quinalphos, ribavirin salithion, sebufos, silafluofen, spinosad, spirodiclofen, spiromesifen, sulfotep, sulprofos, tau-fluvalinate, tebufenozide, tebufenpyrad, tebupirimphos, teflubenzuron, tefluthrin, temephos, temivinphos, terbufos, tetrachlorvinphos, theta-cypermethrin, thiacloprid, thiamethoxam, thiapronil, thiatriphos, thiocyclam hydrogenoxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii* YI 5302 zeta-cypermethrin, zolaprofos (1R-cis)-[5-(phenylmethyl)-3-furanyl]-methyl 3-[(dihydro-2-oxo-3(2H)-furanylidene)methyl]-2,2-dimethylcyclopropanecarboxylate (3-phenoxyphenyl)methyl 2,2,3,3-tetramethylcyclopropanecarboxylate 1-[(2-chloro-5-thiazolyl)methyl]tetrahydro-3,5-dimethyl-N-nitro-1,3,5-triazine-2(1H)-imine 2-(2-chloro-6-fluorophenyl)-4-[4-(1,1-dimethylethyl)phenyl]-4,5-dihydrooxazole 2-(acetyloxy)-3-dodecyl-1,4-naphthalenedione 2-chloro-N-[[[4-(1-phenylethoxy)phenyl]amino]carbonyl]benzamide 2-chloro-N-[[[4-(2,2-dichloro-1,1-difluoroethoxy)phenyl]amino]carbonyl]benzamide 3-methylphenyl propylcarbamate 4-[4-(4-ethoxyphenyl)-4-methylpentyl]-1-fluoro-2-phenoxybenzene 4-chloro-2-(1,1-dimethylethyl)-5-[[2-(2,6-dimethyl-4-phenoxyphenoxy)ethyl]thio]-3(2H)-pyridazinone 4-chloro-2-(2-chloro-2-methylpropyl)-5-[(6-iodo-3-pyridinyl)methoxy]-3(2H)-pyridazinone 4-chloro-5-[(6-chlor-3-pyridinyl)methoxy]-2-(3,4-dichlorophenyl)-3(2H)-pyridazinone

*Bacillus thuringiensis* strain EG-2348

N-[2-benzoyl-1-(1,1-dimethylethyl)]benzohydrazide 2,2-dimethyl-3-(2,4-dichlorophenyl)-2-oxo-1-oxaspiro[4.5]dec-3-en-4-yl butanoate N-[3-[(6-chloro-3-pyridinyl)methyl]-2-thiazolidinylidene]cyanamide dihydro-2-(nitromethylene)-2H-1,3-thiazine-3(4H)-carboxaldehyde ethyl [2-[[1,6-dihydro-6-oxo-1-(phenylmethyl)-4-pyridazinyl]oxy]ethyl]carbamate N-(3,4,4-trifluoro-1-oxo-3-butenyl)glycine N-(4-chlorophenyl)-3-[4-(difluoromethoxy)phenyl]-4,5-dihydro-4-phenyl-1H-pyrazole-1-carboxamide N-methyl-N'-(1-methyl-2-propenyl)-1,2-hydrazinedicarbothioamide N-methyl-N'-2-propenyl-1,2-hydrazinedicarbothioamide O,O-diethyl[2-(dipropylamino)-2-oxoethyl]ethylphosphoramidothioate A mixture with other known active compounds such as herbicides, or with fertilizers and growth regulators, is also possible.

When used as insecticides, the active compound combinations according to the invention in commercially available formulations and in the use forms which are prepared from these formulations may furthermore be present as a mixture with synergists. Synergists are compounds by which the action of the active compounds is increased without it being necessary for the synergist added to be active itself.

The active compound content of the use forms prepared from the commercially available formulations can vary within wide ranges. The active compound concentration of the use forms can amount to from 0.0000001 to 95% by weight of active compound, preferably between 0.0001 and 1% by weight.

They are applied in a customary manner adapted to suit the use forms.

When applied against hygiene and stored-product pests, the active compound combinations are distinguished by outstanding residual action on wood and clay and by good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, scab mites, harvest mites, flies (stinging and licking), parasitic fly larvae, lice, hair lice, bird lice and fleas. These parasites include:

From the order of the *Anoplurida*, for example, *Haematopinus* spp., *Linognathus* spp., *Pediculus* spp., *Phtirus* spp., *Solenopotes* spp.

From the order of the *Mallophagida* and the suborders *Amblycerina* and *Ischnocerina*, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order *Diptera* and the suborders *Nematocerina* and *Brachycerina*, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the *Siphonapterida*, for example, *Pulex* spp., *Ctenocephalides* spp., *Xenopsylla* spp., *Ceratophyllus* spp.

From the order of the *Heteropterida*, for example, *Cimex* spp., *Triatoma* spp., *Rhodnius* spp., *Panstrongylus* spp.

From the order of the *Blattarida*, for example, *Blatta orientalis, Periplaneta americana, Blattella germanica, Supella* spp.

From the subclass of the *Acari* (Acarina) and the orders of the *Metastigmata* and the *Mesostigmata*, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the *Actinedida* (Prostigmata) and *Acaridida* (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations according to the invention are also suitable for controlling arthropods which infest agricultural productive livestock such as, for example, cattle, sheep, goats, horses, pigs, donkeys, camels, buffaloes, rabbits, chickens, turkeys, ducks, geese, honeybees, other domestic animals such as, for example, dogs, cats, caged birds, aquarium fish and what are known as experimental animals, such as, for example, hamsters, guinea pigs, rats and mice. By controlling these arthropods, cases of death and reduced productivity (of meat, milk, wool, hides, eggs, honey and the like) should be diminished, so that more economic and simpler animal husbandry is possible by using the active compound combinations according to the invention.

The active compound combinations according to the invention are applied in the veterinary sector in a known manner by enteral administration in the form of, for example, tablets, capsules, potions, drenches, granules, pastes, boluses, the feed-through method, and suppositories, by parenteral administration, such as, for example, by injections (intramuscular, subcutaneous, intravenous, intraperitoneal and the like), implants, by nasal administration, by dermal use in the form of, for example, dipping or bathing, spraying, pouring on and spotting on, washing, dusting, and with the aid of active-compound-containing moulded articles such as collars, ear marks, tail marks, limb bands, halters, marking devices and the like.

When used on livestock, poultry, domestic animals and the like, the active compounds may be used as formulations (for example powders, emulsions, flowables) which contain the active compounds in an amount of from 1 to 80% by weight, either directly or after 100- to 10000-fold dilution, or they may be used as a chemical bath.

Moreover, it has been found that the active compound combinations according to the invention show a potent insecticidal action against insects which destroy industrial materials.

The following insects may be mentioned by way of example and with preference, but not by way of limitation:

Beetles such as

*Hylotrupes bajulus, Chlorophorus pilosis, Anobium punctatum, Xestobium rufovillosum, Ptilinus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans such as

*Sirex juvencus, Urocerus gigas, Urocerus gigas taignus, Urocerus augur.*

Termites such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails such as *Lepisma saccharina.*

Industrial materials in the present context are understood as meaning non-live materials such as, preferably, plastics, adhesives, glues, paper and board, leather, wood, timber products and paints.

The material which is to be protected from insect attack is very especially preferably wood and timber products.

Wood and timber products which can be protected by the composition according to the invention, or mixtures comprising it, are to be understood as meaning, for example:

Construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of from 0.0001 to 95% by weight, in particular 0.001 to 60% by weight.

The amount of the compositions or concentrates employed depends on the species and the abundance of the insects and on the medium. The optimal quantity to be employed can be determined in each case by test series upon application. In general, however, it will suffice to employ from 0.0001 to 20% by weight, preferably 0.001 to 10% by weight, of the active compound, based on the material to be protected. A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils which are advantageously used are those with a boiling range of from 170 to 220° C., white spirit with a boiling range of from 170 to 220° C., spindle oil with a boiling range of from 250 to 350° C., petroleum and aromatics with a boiling range of from 160 to 280° C., oil of turpentine, and the like.

In a preferred embodiment, liquid aliphatic hydrocarbons with a boiling range of from 180 to 210° C. or high-boiling mixtures of aromatic and aliphatic hydrocarbons with a boiling range of from 180 to 220° C. and/or spindle oil and/or monochloronaphthalene, preferably α-monochloronaphthalene, are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture likewise has an evaporation number of above 35 and a flash point of above 30° C., preferably above 45° C., and that the insecticide/fungicide mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace from 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl)adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, also water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

If appropriate, the ready-to-use compositions may additionally also contain further insecticides and also, if appropriate, one or more fungicides.

The active compound combinations according to the invention can at the same time be employed for protecting objects which come into contact with saltwater or brackish water, such as hulls, screens, nets, buildings, moorings and signalling systems, from fouling.

Fouling by sessile *Oligochaeta*, such as *Serpulidae*, and by shells and species from the *Ledamorpha* group (goose barnacles), such as various *Lepas* and *Scalpellum* species, or by species from the *Balanomorpha* group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile *Entomostraka* groups, which come under the generic term *Cirripedia* (cirriped crustaceans), is of particular importance.

Surprisingly, it has now been found that the active compound combinations according to the invention have an outstanding antifouling action.

Using the active compound combinations according to the invention, the use of heavy metals such as, for example, in bis(trialkyltin)sulphides, tri-n-butyltin laurate, tri-n-butyltin chloride, copper(I)oxide, triethyltin chloride, tri-n-butyl(2-phenyl-4-chlorophenoxy)tin, tributyltin oxide, molybdenum disulphide, antimony oxide, polymeric butyl titanate, phenyl (bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I)ethylene-bisdithiocarbamate, copper thiocyanate, copper naphthenate and tributyltin halides can be dispensed with, or the concentration of these compounds substantially reduced.

If appropriate, the ready-to-use antifouling paints can additionally contain other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propynyl butylcarbamate, tolylfluanid and azoles such as azaconazole, cyproconazole, epoxyconazole, hexaconazole, metconazole, propiconazole and tebuconazole;
molluscicides such as
Fe complexing agents, fentin acetate, metaldehyde, methiocarb, niclosamid, thiodicarb and trimethacarb;
or conventional antifouling active compounds such as
4,5-dichloro-2-octyl-4-isothiazolin-3-one, diiodomethylparatryl sulphone, 2-(N,N-di-methylthiocarbamoylthio)-5-nitrothiazyl; potassium, copper, sodium and zinc salts of 2-pyridinethiol 1-oxide, pyridine-triphenylborane, tetrabutyldistannoxane, 2,3,5,6-tetrachloro-4-(methylsulphonyl)pyridine, 2,4,5,6-tetrachloroisophthalonitrile, tetramethylthiuram disulphide and 2,4,6-trichlorophenylmaleimide.

The antifouling compositions used contain the active compound in a concentration of from 0.001 to 50% by weight, in particular 0.01 to 20% by weight.

Moreover, the antifouling compositions contain the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal and insecticidal active compounds, antifouling paints contain, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably soluble in salt water. Paints may furthermore comprise materials such as colophonium to allow controlled release of the active compounds. Furthermore, the paints may comprise plasticizers, modifiers which affect the rheological properties and other conventional constituents. The active compound combinations may also be incorporated into self-polishing antifouling systems.

The active compound combinations according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the *Scorpionidea*, for example, *Buthus occitanus*.

From the order of the *Acarina*, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the *Araneae*, for example, *Aviculariidae, Araneidae.*

From the order of the *Opiliones*, for example, *Pseudoscorpiones chelifer, Pseudoscorpiones cheiridium, Opiliones phalangium.*

From the order of the *Isopoda*, for example, *Oniscus asellus, Porcellio scaber.*

From the order of the *Diplopoda*, for example, *Blaniulus guttulatus, Polydesmus* spp.

From the order of the *Chilopoda*, for example, *Geophilus* spp.

From the order of the *Zygentoma*, for example, *Ctenolepisma* spp., *Lepisma saccharina, Lepismodes inquilinus.*

From the order of the *Blattaria*, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the *Saltatoria*, for example, *Acheta domesticus.*

From the order of the *Dermaptera*, for example, *Forficula auricularia.*

From the order of the *Isoptera*, for example, *Kalotermes* spp., *Reticulitermes* spp.

From the order of the *Psocoptera*, for example, *Lepinatus* spp., *Liposcelis* spp.

From the order of the *Coleptera*, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the *Diptera*, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the *Lepidoptera*, for example, *Achroia grisella, Galleria mellonella, Plodia interpunctella, Tinea cloacella, Tinea pellionella, Tineola bisselliella.*

From the order of the *Siphonaptera*, for example, *Ctenocephalides canis, Ctenocephalides felis, Pulex irritans, Tunga penetrans, Xenopsylla cheopis.*

From the order of the *Hymenoptera*, for example, *Camponotus herculeanus, Lasius fuliginosus, Lasius niger, Lasius umbratus, Monomorium pharaonis, Paravespula* spp., *Tetramorium caespitum.*

From the order of the *Anoplura*, for example, *Pediculus humanus capitis, Pediculus humanus corporis, Phthirus pubis.*

From the order of the *Heteroptera*, for example, *Cimex hemipterus, Cimex lectularius, Rhodinus prolixus, Triatoma infestans.*

Application in the field of the domestic insecticides can also be effected in combination with other suitable active compounds such as phosphoric esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

When applying the active compound combinations according to the invention, the application rates can be varied within a substantial range, depending on the type of application. In the treatment of plant parts, the application rates of active compound combinations are generally between 0.1 and 10 000 g/ha, preferably between 10 and 1 000 g/ha.

The good insecticidal and acaricidal action of the active compound combinations according to the invention can be seen from the examples which follow. While the individual active compounds exhibit weaknesses with regard to the action, the combinations demonstrate an action which exceeds the simple summation of action.

Insecticides and acaricides always exhibit a synergistic effect when the action of the active compound combination exceeds the sum of the actions of the active compounds when applied individually.

Formula for Calculating the Synergistic Action of a Combination of Two Active Compounds The action to be expected for a given combination of two active compounds can be calculated as follows (cf. Carpenter, C. S., "Mammalian Toxicity of 1-Naphthyl-N-methylcarbamate [Sevin Insecticide]", Agricultural and Food Chemistry, Vol. 9, No. 1, pages 30-39, 1961):

If

Pa stands for the proportion of active compound A,

Pb' stands for the proportion of active compound B, $LC_{50\ (or\ 95)}a$ indicates the concentration at which 50% (or 95%, respectively) of the specimens treated with active compound A are destroyed and $LC_{50\ (or\ 95)}b$ indicates the concentration at which 50% (or 95%, respectively) of the specimens treated with active compound B are destroyed, then the expected $$LC_{50(or.95)}(comb.) = \frac{1}{\frac{Pa}{LC_{50(or95)}\,a} + \frac{Pb}{LC_{50(or95)}\,b}}$$

If the calculated $LC_{50\ (or\ 95)}$ exceeds the value which has actually been achieved and is above the confidence interval, the combination displays superadditive action, i.e. a synergistic effect is present.

USE EXAMPLES

Example A

Plutella Test, Sensitive Strain

| Solvent: | 7 parts by weight of dimethylformamide |
|---|---|
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted to the desired concentration with emulsifier-containing water.

Cabbage leaves (*Brassica oleracea*) are treated by being dipped into the active compound preparation of the desired concentration and are populated with diamond-back moth caterpillars (*Plutella xylostella*, sensitive strain) while the leaves are still moist.

After the desired period, the destruction in % is determined. 100% means that all of the caterpillars have been destroyed; 0% means that no caterpillars have been destroyed. The destruction values determined are calculated using Carpenter's formulae (see previous page).

In this test, a synergistically increased activity in comparison with the active compounds used individually was shown by the following active compound combination in accordance with the present application:

TABLE A

| plant-damaging insects<br>*Plutella* test, sensitive strain | |
|---|---|
| Active compounds | LC$_{50}$ after 6 days |
| Emamectin benzoate | 0.031 ppm |
| Dinotefuran | 27.262 ppm |
| Emamectin benzoate +<br>Dinotefuran (1:125)<br>according to the invention | |
| calc.** | 3.401 ppm |
| found* | 0.021 ppm | found* = found effect
calc.** = effect calculated using Carpenter's formula

Example B

Plutella Test, Resistant Strain

| Solvent: | 7 parts by weight of dimethylformamide |
|---|---|
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted to the desired concentration with emulsifier-containing water.

Cabbage leaves (*Brassica oleracea*) are treated by being dipped into the active compound preparation of the desired concentration and are populated with diamond-back moth caterpillars (*Plutella xylostella*, resistant strain) while the leaves are still moist.

After the desired period, the destruction in % is determined. 100% means that all of the caterpillars have been destroyed; 0% means that no caterpillars have been destroyed. The destruction values determined are calculated using Carpenter's formula.

In this test, a synergistically increased activity in comparison with the active compounds used individually was shown by the following active compound combination in accordance with the present application:

TABLE B

| plant-damaging insects<br>*Plutella* test, resistant strain | |
|---|---|
| Active compounds | LC$_{50}$ after 6 days |
| Emamectin benzoate<br>known | 0.174 ppm |
| Dinotefuran<br>known | 27.621 ppm |
| Emamectin benzoate +<br>Dinotefuran (1:125)<br>according to the invention | |
| calc.** | 12.195 ppm |
| found* | 0.030 ppm | found* = found effect
calc.** = effect calculated using Carpenter's formula

Example C

Heliothis Armigera Test

| Solvent: | 7 parts by weight of dimethylformamide |
|---|---|
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted to the desired concentration with emulsifier-containing water.

Soya bean shoots (*Glycine max*) are treated by being dipped into the active compound preparation of the desired concentration and are populated with *Heliothis armigera* caterpillars while the leaves are still moist.

After the desired period, the destruction in % is determined. 100% means that all of the caterpillars have been destroyed; 0% means that no caterpillars have been destroyed. The destruction values determined are calculated using Carpenter's formula.

In this test, a synergistically increased activity in comparison with the active compounds used individually was shown by the following active compound combination in accordance with the present application:

TABLE C

| | plant-damaging insects<br>*Heliothis armigera* test |
|---|---|
| Active compounds | LC$_{50}$ after 6 days |
| Avermectin<br>known | 0.014 ppm |
| Dinotefuran<br>known | 13.165 ppm |
| Avermectin + Dinotefuran (1:5)<br>in accordance with the invention | |
| calc.** | 0.083 ppm |
| found* | 0.022 ppm | found* = found effect
calc.** = effect calculated using Carpenter's formula

Example D

Phaedon Larvae Test

| Solvent: | 7 parts by weight of dimethylformamide |
|---|---|
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted to the desired concentration with emulsifier-containing water.

Cabbage leaves (*Brassica oleracea*) are treated by being dipped into the active compound preparation of the desired concentration and are populated with mustard beetle larvae (*Phaedon cochleariae*) while the leaves are still moist.

After the desired period, the destruction in % is determined. 100% means that all of the beetle larvae have been destroyed; 0% means that no beetle larvae have been destroyed. The destruction values determined are calculated using Carpenter's formula.

In this test, a synergistically increased activity in comparison with the active compounds used individually was shown by the following active compound combination in accordance with the present application:

TABLE D

| | plant-damaging insects<br>*Phaedon* larvae test |
|---|---|
| Active compounds | LC$_{95}$ after 3 days |
| Avermectin<br>known | 0.281 ppm |
| Dinotefuran<br>known | 42.07 ppm |
| Avermectin + Dinotefuran (1:5)<br>in accordance with the invention | |
| calc.** | 1.629 ppm |
| found* | 0.893 ppm | found* = found effect
calc.** = effect calculated using Carpenter's formula

Example E

Spodoptera Frugiperda Test

| Solvent: | 7 parts by weight of dimethylformamide |
|---|---|
| Emulsifier: | 2 parts by weight of alkylaryl polyglycol ether |

To prepare a suitable active compound preparation, 1 part by weight of active compound is mixed with the stated amounts of solvent and emulsifier, and the concentrate is diluted to the desired concentration with emulsifier-containing water.

Cabbage leaves (*Brassica oleracea*) are treated by being dipped into the active compound preparation of the desired concentration and are populated with army worm caterpillars (*Spodoptera frugiperda*) while the leaves are still moist.

After the desired period, the destruction in % is determined. 100% means that all of the caterpillars have been destroyed; 0% means that no caterpillars have been destroyed. The destruction values determined are calculated using Carpenter's formula.

In this test, a synergistically increased activity in comparison with the active compounds used individually was shown by the following active compound combination in accordance with the present application:

TABLE E

| | plant-damaging insects<br>*Spodoptera frugiperda* test |
|---|---|
| Active compounds | LC$_{50}$ after 6 days |
| Avermectin<br>known | 5.553 ppm |
| Dinotefuran<br>known | 2.861 ppm |
| Avermectin +<br>Dinotefuran (1:5)<br>according to the invention | |
| calc.** | 3.115 ppm |
| found* | 0.6 ppm | found* = found effect
calc.** = effect calculated using Carpenter's formula

What is claimed is:

1. A composition for controlling animal pests comprising a synergistically active mixture of dinotefuran of formula (I)

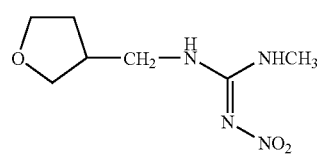

and abamectin.

2. The composition of claim 1 wherein said animal pests are caterpillars.

3. The composition of claim 2 wherein said animal pests are selected from *Heliothis armigera* caterpillars and army worm caterpillars (*Spodoptera frugiperda*).

4. A process for the preparation of pesticides comprising mixing a synergistically active mixture according to claim 1 with one or more extenders and/or surfaceactive substances.

5. A composition for controlling animal pests comprising a synergistically active mixture of dinotefuran of formula (I)

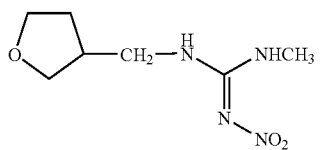

and abamectin wherein said animal pests are army worm caterpillars (*Spodoptera frugiperda*).

6. A process for the preparation of pesticides comprising mixing a synergistically active mixture according to claim 5 with one or more extenders and/or surfaceactive substances.

7. A method of controlling animal pests comprising applying a composition for controlling animal pests comprising a synergistically active mixture of dinotefuran of formula (I)

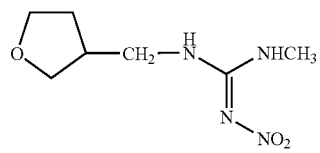

and abamectin to animal pests and/or a material to be protected from the animal pests, wherein said animal pests are army worm caterpillars (*Spodoptera frugiperda*).

* * * * *